United States Patent [19]

Rink

[11] Patent Number: 5,057,099

[45] Date of Patent: Oct. 15, 1991

[54] METHOD FOR LASER SURGERY

[75] Inventor: John L. Rink, San Francisco, Calif.

[73] Assignee: Xintec Corporation, Oakland, Calif.

[21] Appl. No.: 523,473

[22] Filed: May 14, 1990

Related U.S. Application Data

[63] Continuation-in-part of Ser. No. 265,565, Nov. 1, 1988, Pat. No. 4,950,268, which is a continuation-in-part of Ser. No. 19,755, Feb. 27, 1987.

[51] Int. Cl.⁵ ............................................... A61N 5/06
[52] U.S. Cl. ...................................... 606/12; 606/15; 606/16; 128/398; 128/898
[58] Field of Search ............... 128/395, 397, 398, 898; 606/10-18; 356/73.1; 219/121.83

[56] References Cited

U.S. PATENT DOCUMENTS

| | | | |
|---|---|---|---|
| 4,543,477 | 9/1985 | Doi et al. | 606/12 |
| 4,950,268 | 8/1990 | Rink | 606/12 |

FOREIGN PATENT DOCUMENTS 212786  3/1987  European Pat. Off. ............. 606/12

Primary Examiner—David Shay
Attorney, Agent, or Firm—Howard Cohen

[57] ABSTRACT

A method for carrying out surgical procedures using a laser and a laser surgical tool includes the provision of a temperature control device associated with the laser which monitors the temperature of the surgical tool and delivery system and governs the laser power output to achieve a desired temperature level. The temperature control device may be used either to prevent heating of the surgical tool and delivery system beyond it structural tolerance, or to maintain a predetermined temperature level which is optimized for a particular surgical or medical procedure. The delivery system may comprise an optical fiber, and the surgical tool may comprise the output end of the optical fiber which is free of any additional surgical cutting implement.

8 Claims, 1 Drawing Sheet

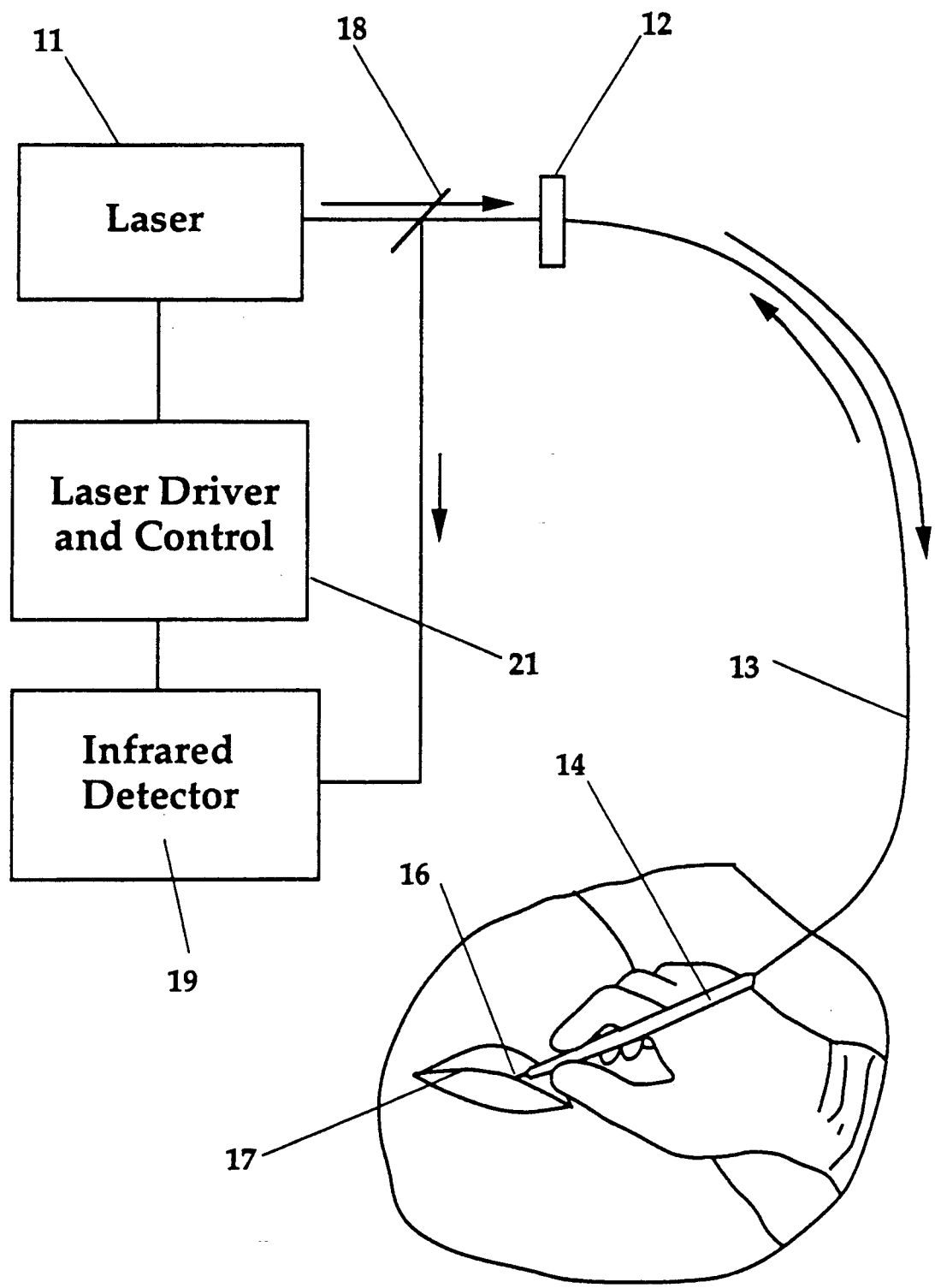

METHOD FOR LASER SURGERY

REFERENCE TO RELATED APPLICATION

This application is a continuation-in-part of application Ser. No. 07/265,565, filed Nov. 1, 1988, now U.S. Pat. No. 4,950,268 issued Aug. 21, 1990 to John Rink, which is a continuation-in-part of application Ser. No. 07/019,755, filed Feb. 27, 1987, for which priority is claimed.

BACKGROUND OF THE INVENTION

In recent years the field of medicine has witnessed the application of lasers for therapeutic treatment of a variety of diseases and conditions. Laser energy conducted through a flexible waveguide such as an optical fiber has been used successfully for hemostasis, photodynamic destruction of some forms of tumors, removal of epidermal growths and abnormalities, and the like.

Lasers have also been adapted for use in surgical procedures, and surgical devices have been built, tested, and sold commercially. However, some drawbacks in laser devices for surgical use have been noted in the prior art. For example, U.S. Pat. Nos. 4,693,244 and 4,736,743 discuss the use of a bare optical fiber connected to a laser and used to cut tissue. It is noted that if the bare fiber end contacts the tissue being cut, the fiber becomes fouled, the transmission efficiency decreases, more heat is generated in the fiber, thermal runaway ensues, and the fiber quickly heats to the point of material failure. One attempted solution to this problem in the prior art is to use the fiber end in a non-contact mode, thereby avoiding contamination of the fiber output end. However, contamination is difficult to avoid in practice, due to the fact that the fiber must be held very close to the tissue target, and tissue contact is unavoidable. A single contact with tissue will often result in fiber failure. Also, the smoke and vapor arising from the laser beam impact site can contaminate the fiber end without any contact with the tissue itself.

Another attempt to solve this problem has been the provision of a transparent tip secured to the output end of the optical fiber, the tip being formed of a material such as sapphire that is tolerant of extremely high temperatures. If the tip becomes fouled or coated with carbonized material, it will not be heated to the point of material failure. Several manufacturers make available surgical optical tips having differing cutting configurations. However, even sapphire can be fractured by the high temperatures and temperature transitions experienced at the optical fiber output end. Moreover, sapphire or any similar material is expensive and difficult to manufacture, and the surgical tips can be reused only a few times.

A surgical tip, as well as a bare optical fiber end, may be subject to a constant flow of gas or liquid to cool the heated end and to remove some of the inevitable contamination. In some procedures, gas cooling can create the risk of embolism in the patient, and liquid cooling can cause such problems as fluid distension, fluid absorption through the surgical wound, and the like.

The simplest practical solution available in state of the art surgical lasers is to limit the laser power to a level that cannot damage the optical fiber. Ironically, this approach requires that a laser capable of delivering high power; e.g., 120 watts of beam energy, must often be limited to 30 or 40 watts output to preserve the optical fiber integrity. Alternatively, the optical fiber output end must be constantly immersed in a laser-transparent liquid, such as water, during operation, or the tip must remain in contact with the tissue during operation so that the tissue cools the fiber tip. This conditions are difficult to achieve in practice.

SUMMARY OF THE PRESENT INVENTION

The present invention generally comprises a method for carrying out surgical procedures using an optical fiber heated by a laser beam transmitted therethrough as the surgical tool. A salient feature of the invention is the provision of a temperature control device associated with the laser which monitors the temperature of the optical fiber and governs the laser power output to achieve a desired temperature level in the optical fiber. The temperature control device may be used to prevent heating of the optical fiber beyond its structural tolerance. Thus the problems known in the prior art associated with contamination of the optical fiber output end, and the resulting thermal runaway, are obviated, and the use of expensive laser surgical cutting tips is eliminated. The optical fiber output end may also be maintained at a predetermined temperature level which is optimized for a particular surgical or medical procedure.

The temperature control device may comprise a light sensitive diode or other photosensitive detector that is designed to respond to the infrared radiation that is emitted by heated bodies. The detector is preferably located within the laser and disposed to monitor the laser beam path. As is known in the prior art, the detector may be placed in the reflective path of a partially silvered mirror or beam splitter which is located in the laser output beam path. The laser output is typically delivered to a surgical site by a flexible optical fiber or an articulated tubular arm; the detector monitors the delivery system and senses any infrared radiation returning through the delivery system and the associated optical components.

For example, when the infrared radiation exceeds a predetermined threshold indicative of an unacceptably high temperature within the beam delivery path, the detector signal exceeds a threshold and trips a laser control circuit. This arrangement is described in application Ser. No. 07/265,565, filed Nov. 1, 1988, now U.S. Pat. No. 4,950,268, issued Aug. 21, 1990 to John Rink. The threshold temperature may be set below the temperature at which the optical fiber material is damaged. Thus, for example, if the optical fiber output end is used to cut, ablate, or coagulate, and becomes coated with debris or carbonized material, the contaminating material will cause absorption of laser radiation at the fiber end and a localized hot spot. When the hot spot temperature approaches the threshold of thermal damage to the optical fiber, the laser energy is reduced by the trip circuit before the fiber can be damaged. The laser power is cut back to a level which continues operation but does not damage the fiber. After a short time, the continued operation usually causes the contaminants to burn away, the infrared signal diminishes, and operation at the desired power level resumes automatically.

Alternatively, in a laser surgical apparatus having an optical fiber delivery system with an output end that is heated by the laser beam passing therethrough, the detector signal may be used to control the laser output power so that the output end is maintained at a preset temperature that is optimum for the procedure being undertaken.

BRIEF DESCRIPTION OF THE DRAWING

The FIGURE is a functional block diagram of a method for laser surgery using a bare optical fiber output end as the surgical instrument and a temperature control device to control the surgical laser.

DESCRIPTION OF THE PREFERRED EMBODIMENT

The present invention generally comprises a method for laser surgery. With regard to the Figure, the invention includes a laser 11 adapted for surgical use, such as a Nd:YAG, $CO_2$, Argon, dye laser, or other form of laser known in the prior art for surgical use. The laser 11 typically includes a standard coupling device 12 through which the laser delivers a beam of laser energy to an optical fiber delivery system 13. The coupling device 12 is typically an SMA or STC releasable connector. The delivery system may comprise a hollow waveguide, or an articulated arm delivery system, rather than an optical fiber system. The delivery system 13 conducts the laser energy to a surgical cutting instrument 14 having a cutting tip 16.

In its simplest form, the delivery system 13 employs an optical fiber that extends through a hollow stylet comprising the surgical cutting instrument 14. The distal end of the optical fiber may comprise the cutting tip 16, with the distal end portion of the cladding of the optical fiber being stripped away to expose a small portion of the circumferential surface of the fiber adjacent to the distal end.

Alternatively, the distal end of the cutting instrument 14 may be provided with a laser surgical cutting tip optically coupled to the output of the delivery system 13. However, it should be noted that a separate cutting tip is not necessary, but may be provided to satisfy the personal preference of individual surgeons.

Interposed between the laser 11 and the coupling 12 is a beam splitter or partially reflective mirror 18 disposed in the laser beam path. The mirror 18 is configured to reflect infrared radiation, and is oriented to reflect infrared radiation from the delivery system 13 toward an infrared detector 19. The infrared detector generates a signal which is indicative of the magnitude of the infrared radiation received by the detector, and this signal is conducted to a laser driver and control circuit 21. The infrared detector 19 and laser driver and control circuit 21 are described in in application Ser. No. 07/265,565, filed Nov. 1, 1988, now U.S. Pat. No. 4,950,268, issued Aug. 21, 1990 to John Rink, which is incorporated herein by reference. As described in that patent, the laser is driven to deliver pulses of laser energy, and the infrared detector signal is monitored during the interval between consecutive pulses to obtain a temperature reading in the beam path, which includes the delivery system and surgical instrument. The detector signal is employed by the driver and control circuit 21 to determine the duration of the subsequent laser pulse; as the difference between the infrared signal magnitude and a predetermined level increases, the laser pulses are decremented in duration, and vice versa. In this manner the average power output of the laser is varied to provide a constant temperature reading. This system provides excellent results, both in maintaining a desired temperature in the surgical instrument and in limiting the temperature within the delivery path to a level which is below the threshold of thermal damage to any components. Other laser temperature control arrangements are known in the prior art, and the present invention is intended for general use with any laser having a temperature control feature that is functionally equivalent. (It should be noted that it is within the level of ordinary skill in the art to employ a continuous, or CW laser, and to periodically interrupt the laser output for a brief time while the infrared return from the delivery system is detected to determine the temperature level in the delivery system.)

The stylet 14 is wielded by the surgeon so that the optical fiber distal end 16 is drawn across the tissue to be cut, forming an incision 17. It may be appreciated that the temperature of the cutting end 16 is controlled in real time, so that, e.g., as the end 16 is removed from the incision and the laser is operating, the temperature of the end 16 begins to increase due to the cessation of cooling effect of tissue contact, and the power of the laser is reduced to prevent overheating of the end 16. Likewise, the end 16 may be used to coagulate blood or other bodily fluids without contacting the fluid or surrounding tissue, due to the fact that the temperature control system protects the optical fiber 13 and the end 16 from overheating. Furthermore, the system is capable of ablating or vaporizing plaque, such as atherosclerotic deposits. In all of these procedures, there is no need for fluid or liquid flow around or past the end 16 for cooling or cleansing effect. Moreover, the system may be used to cut or coagulate while immersed in liquid, such as transparent saline, Ringer's solution, or the like.

I claim:

1. A method for carrying out surgical procedures using a laser, having an output power, comprising the steps of connecting an optical fiber delivery system to the laser with the output end of the optical fiber at the surgical site, providing an infrared detector disposed to monitor the laser beam output path to receive infrared radiation from the optical fiber delivery system and generate an infrared detector signal, operating the laser and performing surgery with the output end of the optical fiber, and using the infrared detector signal to modulate and continue the power output by the laser to the optical fiber delivery system so that the output end of the optical fiber is maintained within a predetermined temperature range.

2. The method of claim 1, wherein the laser is operated in a repetitive pulse mode, and the infrared detector senses the infrared radiation from the optical fiber delivery system during intervals between laser pulses.

3. The method of claim 1, wherein the laser output power is reduced when the infrared radiation received by the infrared detector exceeds a predetermined threshold.

4. The method of claim 1, further including the step of forming the output end of the optical fiber as a bare end which is free of any surgical cutting accessory.

5. A method for carrying out surgical procedures using a laser, having an output power, comprising the steps of connecting an optical fiber delivery system to the laser with the output end of the optical fiber at the surgical site, providing an infrared detector disposed to monitor the laser beam output path to receive infrared radiation from the optical fiber delivery system and generate an infrared detector signal, operating the laser in a repetitive pulse mode and performing surgery with the output end of the optical fiber, and using the infrared detector to detect the infrared radiation from the optical fiber delivery system during intervals between laser pulses and generate a signal to modulate the power output by the laser to the optical fiber delivery system so that the output end of the optical fiber is maintained within a predetermined temperature range.

6. The method of claim 5, wherein the laser output power is curtailed when the infrared radiation received by the infrared detector exceeds a predetermined threshold.

7. The method of claim 6, wherein a magnitude of the infrared radiation detected after each laser pulse is used to determine a duration of the subsequent laser pulse.

8. The method of claim 7, wherein the difference between the magnitude of the infrared radiation detected after each laser pulse and a preselected magnitude level is used to determine the duration of the subsequent laser pulse, whereby a positive difference causes a reduction in duration of the subsequent laser pulse, and a negative difference causes an increase in the duration of the subsequent laser pulse.

* * * * *